US 6,647,983 B2
Nov. 18, 2003

(54) LOW-PRESSURE VALVE

(75) Inventors: Dexter G. Smith, Columbia, MD (US); Michael P. Boyle, Severna Park, MD (US); Protagoras N. Cutchis, Highland, MD (US); William R. Allmon, Catonsville, PA (US)

(73) Assignee: The Johns Hopkins University, Baltimore, MD (US)

( * ) Notice: Subject to any disclaimer, the term of this patent is extended or adjusted under 35 U.S.C. 154(b) by 325 days.

(21) Appl. No.: 09/681,248

(22) Filed: Mar. 6, 2001

(65) Prior Publication Data

US 2001/0035187 A1 Nov. 1, 2001

Related U.S. Application Data

(60) Provisional application No. 60/190,203, filed on Mar. 17, 2000.

(51) Int. Cl.[7] .................................................. A62B 9/02
(52) U.S. Cl. .............................. 128/205.24; 128/205.11
(58) Field of Search ...................... 128/205.11, 205.24, 128/205.22, 204.26, 204.23, 204.22; 137/625.12, 625.15; 251/206, 207

(56) References Cited

U.S. PATENT DOCUMENTS

| 417,795 A | * | 12/1889 | Starr | 128/205.24 |
|---|---|---|---|---|
| 1,204,004 A | * | 11/1916 | Gilliam | 137/556 |
| 2,106,942 A | * | 2/1938 | Beehler et al. | 137/94 |
| 2,746,430 A | * | 5/1956 | Steen | 91/174 |
| 2,765,809 A | * | 10/1956 | Lamar | 137/625.12 |
| 2,909,197 A | * | 10/1959 | Liley | 138/45 |
| 3,097,642 A | * | 7/1963 | Russell | 128/205.17 |
| 3,419,029 A | * | 12/1968 | Straub | 128/205.24 |
| 3,513,981 A | * | 5/1970 | Mendelow | 210/411 |
| 3,828,932 A | * | 8/1974 | Schneer | 210/169 |
| 3,830,257 A | * | 8/1974 | Metivier | 137/625.41 |
| 3,850,171 A | * | 11/1974 | Ball et al. | 128/204.25 |
| 4,036,253 A | * | 7/1977 | Fegan et al. | 137/556 |
| 4,236,546 A | * | 12/1980 | Manley et al. | 137/88 |
| 4,253,494 A | * | 3/1981 | Cooke | 137/625.23 |
| 4,365,563 A | * | 12/1982 | Wu | 110/186 |
| 4,921,598 A | * | 5/1990 | Desch | 210/136 |
| 4,957,107 A | | 9/1990 | Sipin | 128/204.21 |
| 5,040,532 A | * | 8/1991 | Alfery | 128/207.15 |
| 5,103,814 A | * | 4/1992 | Maher | 128/204.18 |
| 5,218,998 A | | 6/1993 | Bakken et al. | 137/625.28 |
| 5,471,977 A | * | 12/1995 | Olsson et al. | 128/204.22 |
| 5,577,496 A | * | 11/1996 | Blackwood et al. | 128/201.25 |
| 5,694,926 A | | 12/1997 | DeVries et al. | 128/205.24 |
| 5,881,722 A | | 3/1999 | DeVries et al. | 128/204.21 |
| 6,152,135 A | | 11/2000 | DeVries et al. | 128/205.24 |

* cited by examiner

Primary Examiner—Aaron J. Lewis
(74) Attorney, Agent, or Firm—Albert J. Fasulo, II

(57) ABSTRACT

A low-pressure valve enabling precise control of a fluid flow rate through the valve during cyclical operation of the valve. The valve is useful for controlling air delivery to a patient as part of a portable ventilator. The valve comprises a housing having an inlet 16 and two outlets 18 and 20. A wiper plate 22 and an orifice plate 24 are disposed inside of the housing. Transverse movement of the wiper plate 22 relative to the orifice plate 24, powered for example by a servomotor 34, simultaneously and alternatively covers and uncovers various openings 26 in the orifice plate 24. The total flow through the valve is thereby divided between the two outlets 78 and 20.

5 Claims, 3 Drawing Sheets

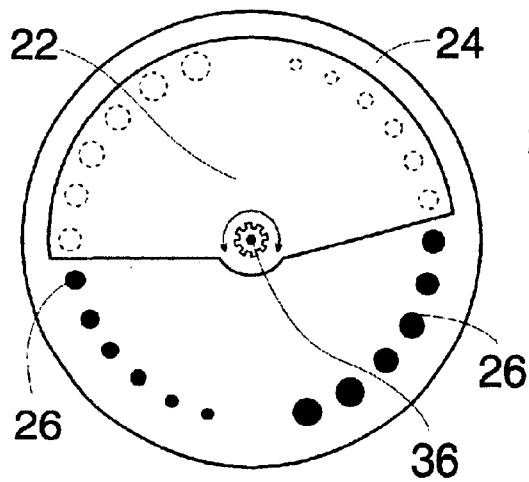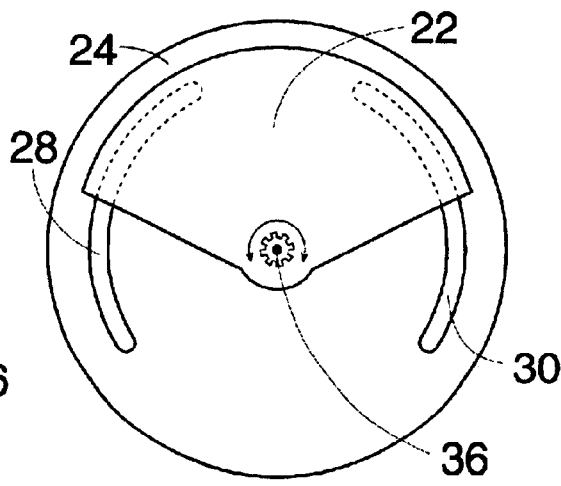
Fig. 2A          Fig. 2B
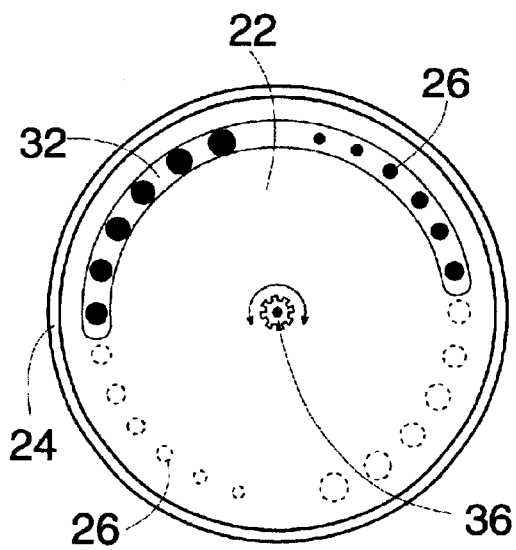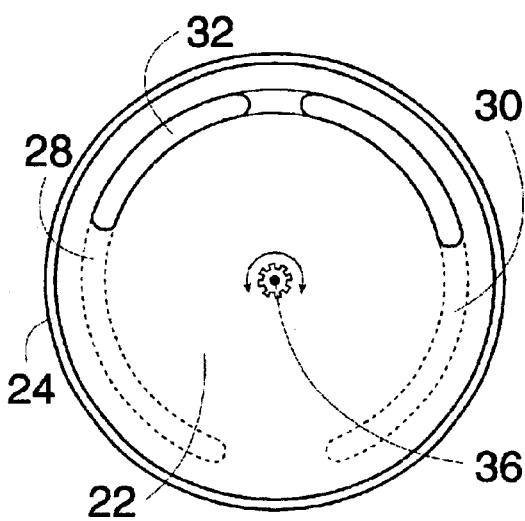
Fig. 2C          Fig. 2D

LOW-PRESSURE VALVE

CROSS REFERENCE TO RELATED APPLICATIONS

This application claims priority of U.S. Provisional Application No. 60/190,203 filed Mar. 17, 2000.

FEDERAL RESEARCH STATEMENT

This invention was made with government support under contract DAMD17-99-2-9041 awarded by the Department of the Army. The government has certain rights in the invention.

BACKGROUND OF INVENTION

The invention relates generally to fluid delivery systems requiring precise quantities of fluid to be metered cyclically, and more specifically to portable ventilators having automated monitoring and regulation.

The medical community has a need for portable ventilators for assisting patients who cannot breathe on their own. Such devices must be lightweight and compact for convenient transportation and use by wheelchair users and by medical first responders such as paramedics and combat medics. Prior art devices have generally been bulky and heavy, often because of the large compressor systems and power supplies needed to provide adequate volumes of air to a patient.

Many portable ventilators use low-pressure variable speed rotary compressors. Such compressors can effectively modulate gas delivery to patients; however, they require relatively large and sophisticated power systems to manage the rapid acceleration and deceleration of the compressor components during a patient's breathing cycles.

Alternatives to variable speed rotary compressors include constant speed rotary compressors or diaphragm compressors. Such compressors are generally lighter weight and use simpler power systems. Constant speed compressors are sized to meet a patient's maximum airflow requirements during inspiration. During expiration or during a reduced rate inspiration, the compressor continues to supply a constant volume of air; however any unneeded air is diverted away from the patient using a flow valve.

Although ventilators with constant speed compressors are lighter weight and require less power, they also present a significant technical challenge concerning the precise cyclical modulation of airflow. To be effective, all ventilators must be capable of delivering precisely calibrated and timed volumes of air to a patient. With variable speed compressors, this is often accomplished using calibrated compressor speed data and patient lung pressure data that are processed by a microcomputer. The microcomputer calculates the delivered air volume by integrating the flow rate. A feedback loop then enables continuous speed control of the compressor. With constant speed compressors, a microcomputer monitors patient lung pressure and the flow rate through the flow valve. However the flow rate through the flow valve is generally non-linear and is a function of both the valve position and the pressure across the valve. Most commercially available valves operate at relatively high pressures between 50 and 100 psi. Precise real-time control of the airflow to the patient can thus be very difficult, particularly when the pressure across the valve changes dramatically with minimal changes in valve position, such as when the valve is nearly closed. Minor hysteresis in the valve position control can thus create significant errors in airflow measurement.

Attempts at solving the above flow rate measurement problem with constant speed compressors include systems that maintain a constant low-pressure across the flow valve. These systems include bypass valves that vent excess airflow either to the atmosphere or back to the compressor intake. The bypass valve prevents excessive backpressure from building up across the flow valve. However these systems are more complex and expensive because they require a precisely calibrated bypass valve as well as a flow valve, and still require the measurement of pressure across the flow valve in order to accurately determine the airflow rate.

A need exists therefore for a better low-pressure valve that enables precise airflow control with a minimum number of parts.

SUMMARY OF INVENTION

The present invention, among other things, presents a solution to the aforementioned problems associated with prior art low-pressure valves.

It is an object of the present invention to provide a low-pressure valve that is free of the stated disadvantages of the prior art.

Another object of the present invention is to provide a low-pressure valve that enables nearly linear control of fluid flow rate through the valve during cyclical operation of the valve.

Yet another object of the present invention is to provide a low-pressure valve for use with a portable ventilator system that includes a constant speed compressor.

An embodiment of the present invention includes a valve housing having an upstream end and a downstream end, the upstream end having at least one fluid inlet and the downstream end having first and second fluid outlets. An orifice plate is disposed in the housing and has a first opening for allowing fluid to flow to the first fluid outlet; the orifice plate also has a second opening for allowing fluid to flow to the second fluid outlet. A wiper plate is disposed parallel to and sealingly adjacent the orifice plate. Transverse motion of the wiper plate relative to the orifice plate at least partially covers the first orifice plate opening while it simultaneously at least partially uncovers the second orifice plate opening.

Other objects and advantages of the invention will become more fully apparent from the following more detailed description and the appended drawings that illustrate several embodiments of the invention. In the following description, the terms fluid, gas and air are interchangeable, and all like reference numerals refer to like elements.

BRIEF DESCRIPTION OF DRAWINGS

FIGS. 2A 2D are top views of the wiper plate and orifice plate according to various embodiments of the present invention.

DETAILED DESCRIPTION

Figure 1:
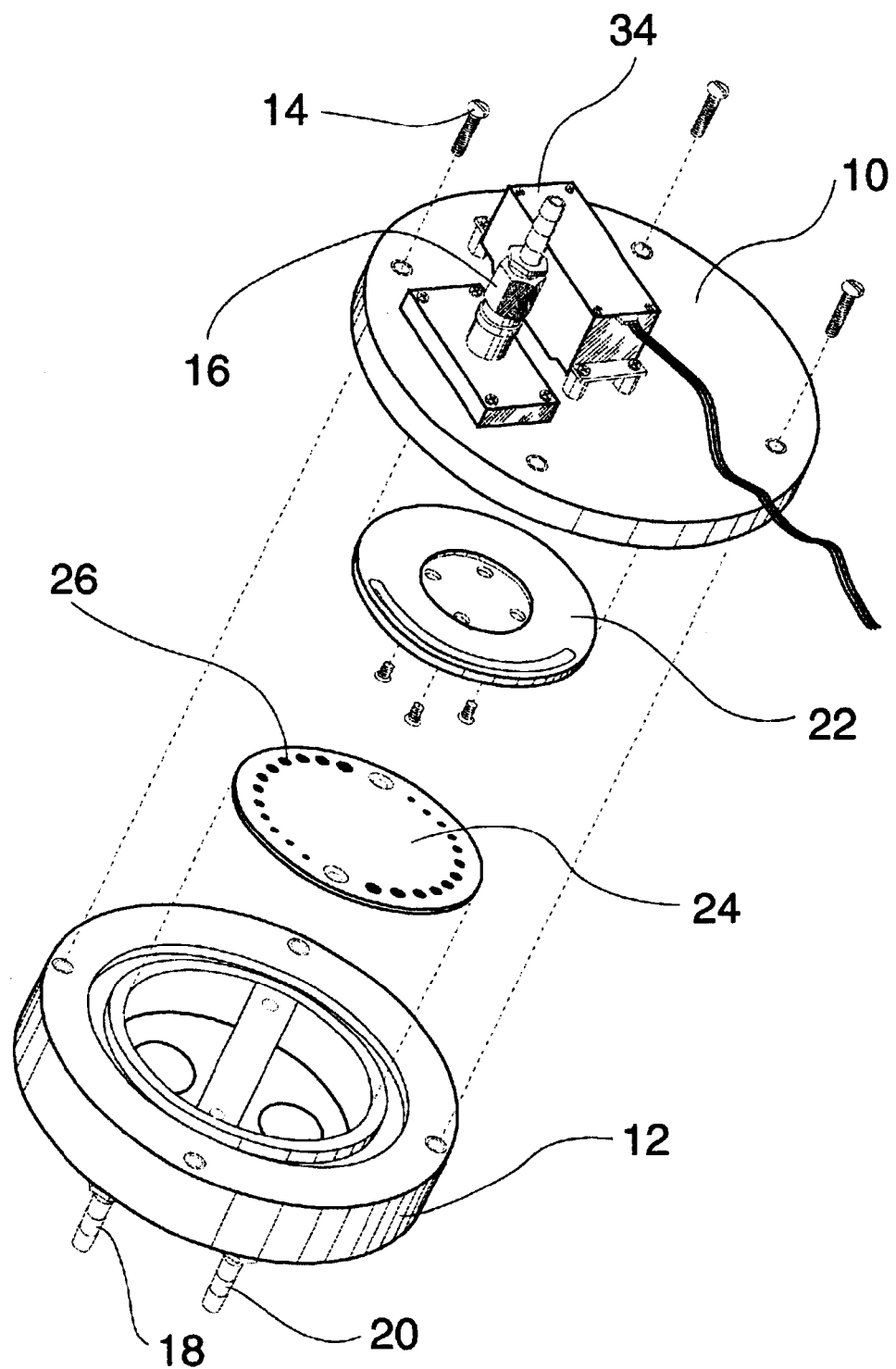
FIG. 1 is an exploded view of an embodiment of the present invention illustrating the interaction among the major components.

FIG. 1 is an exploded view of an embodiment of the present invention. The embodiment includes a valve housing with an upstream end 10 that is attached to a downstream end 12 by a series of fasteners 14. The upstream end 70 includes a fluid inlet 16 that, when used with a portable ventilator system, receives gas from a compressor. After entering the inlet 16, the gas flows past two parallel plates and exhausts through two fluid outlets 18 and 20 in the downstream end 12 of the housing. One of the plates is a wiper plate 22 and the other plate is an orifice plate 24.

In the embodiment shown in FIG. 1 the wiper plate 22 is disposed on top of the orifice plate 24. One half of the orifice plate 24 includes a number of openings 26 that exhaust gas to the first fluid outlet 18 in the downstream end 12 of the valve housing. The other half of the orifice plate 24 includes a similar number of openings 26 that exhaust gas to a second fluid outlet 20 in the downstream end 12 of the valve housing. When used with a portable ventilator, the first fluid outlet 18 is connected to a patient respirator. The second fluid outlet 20 is either vented to the atmosphere or is connected to the inlet of the compressor such that gas exiting the second fluid outlet 20 is recycled back to the valve inlet 16. The latter option is useful, for example, when air moving through the valve is supplemented with oxygen.

The orifice plate 24 and the wiper plate 22 are designed to provide a constant total flow from the two fluid outlets 18 and 20. Such a design maintains a constant load on the compressor and allows the fluid flow through each of the individual valve outlets 18 and 20 to be linearly adjusted. In the embodiment shown in FIG. 1, the wiper plate 22 is disposed adjacent to the orifice plate 24 such that the wiper plate 22 seals closed any covered openings 26 in the orifice plate 24. Transverse motion of the wiper plate 22 alternatively opens and closes selected openings 26, holes in this case, in the orifice plate 24. In this embodiment twelve holes are always uncovered to vent gas to the two outlets 18 and 20. However, depending on the position of the wiper plate 22, more or less gas is metered to each respective outlet. For example, in FIG. 1, if the wiper plate 22 is rotated clockwise, an increasing number of holes in the orifice plate 24 will be exposed over the fluid outlet 18 leading to the patient; simultaneously, an equal number of holes leading to the second fluid outlet 20 will be covered by the wiper plate 22. At an extreme clockwise position, all twelve holes over the first outlet 18 are uncovered and all twelve holes over the second outlet 20 are covered, thus delivering all of the flow from the compressor to the patient. Conversely, for example during patient exhalation, if the wiper plate 22 is positioned in an extreme counterclockwise position, all twelve holes leading to the patient are covered and all of the flow from the compressor is vented to the second fluid outlet 20.

The total cross sectional area of the uncovered holes in the orifice plate 24 remains nearly constant regardless of the position of the wiper plate 22; this enables the total flow through the valve to also remain nearly constant throughout most of a patient's respiratory cycle. A constant total flow through the valve in turn minimizes backpressure upstream of the valve plates 22 and 24, which would otherwise lead to the problems associated with the prior art concerning valve hysteresis and decreased control over the flow of gas to the patient. Note that, in the embodiment shown in FIG. 1, the holes in the orifice plate 24 have increasing and decreasing diameters, respectively, over the first and second fluid outlets 18 and 20. Such a design provides additional control over the flow of gas to a patient. When the first fluid outlet 18 leading to the patient is nearly closed by the wiper plate 22, only the smallest holes in the orifice plate 24 that lead to the patient remain uncovered.

Persons skilled in the art will readily recognize various other embodiments of the invention. For example, FIGS. 2A–2D are top views of various design embodiments of the wiper plate 22 and orifice plate 24. Each of FIGS. 2A–2D is centered on a motor shaft 36 that engages the wiper plate 22. FIG. 2A illustrates an embodiment having a wedge-shaped wiper plate 22 used to cover and uncover various holes in the orifice plate 24. The embodiment shown in FIG. 2B replaces the series of openings 26 in the orifice plate 24 with two elongated slots 28 and 30. FIG. 2C illustrates the same design as that shown in FIG. 1. FIG. 2D illustrates an embodiment using two elongated slots 28 and 30 in the orifice plate 24 and one elongated slot 32 in the wiper plate 22. Still other embodiments of the present invention incorporate, for example, a linear wiper plate 22 that uncovers and covers the openings 26 in the orifice plate 24 through sideways motion of the wiper plate 22.

Another embodiment of the invention enables a user to select and substitute a specific design of the orifice plate 24 depending on the needs of the patient. The ventilator system can include a collection of orifice plates 24 of varying geometries. A larger patient, for example, might require an orifice plate 24 with larger holes enabling greater total flow through the valve. The orifice plate 24 is inexpensive and easy to manufacture and is easily substituted when the valve housing is designed for quick disassembly. Such quick disassembly valve housing designs include the use of snap fit fasteners or other quick release fasteners for connecting the upstream and downstream ends 10 and 12 of the valve housing. The orifice plate 24 may be designed to rest on a shoulder circumscribing the interior of the valve housing such that the orifice plate 24 is easily lifted out of the housing upon disassembly of the valve. Substitution of various orifice plate 24 designs enables the entire ventilator system to be customized to the needs of individual patients without requiring any changes to the valve control and compressor control circuitry.

Motion of the wiper plate 22 can be controlled by various methods including the use of a stepper motor or a servomotor 34. In the embodiment shown in FIG. 1, the servomotor 34 is attached to the upstream end 18 of the valve housing. The motor shaft 36 (shown only in FIGS. 2A–2D) extends through the housing and is connected to the wiper plate 22 such that an angular rotation of the motor shaft 36 results in an equivalent angular rotation of the wiper plate 22. Because the valve design enables linear adjustments to the airflow, and because servomotors have a linear angular displacement versus voltage curve, the airflow to the patient versus voltage to the servomotor 34 is also a linear function. The angular displacement of the servomotor 34 may also be controlled using pulse width modulation.

Use of the present invention in a portable patient ventilator does not require differential pressure measurements across the orifice plate 24. Rather, pressure and flow are measured downstream of the first fluid outlet 18.

The present invention may operate at very low-pressures, often less than one psi, enabling the valve housing and components to be constructed of lightweight materials. One embodiment of the invention uses precision machined aluminum for the housing and orifice plate 24, and Delrin AF (a trademark of the Dupont Corporation) for the wiper plate 22.

The wiper plate 22 and orifice plate 24 are machined and assembled with close tolerances. A separation between the plates 22 and 24 of less than 0.001 inches minimizes air leakage across the plate surfaces.

Figure 3:
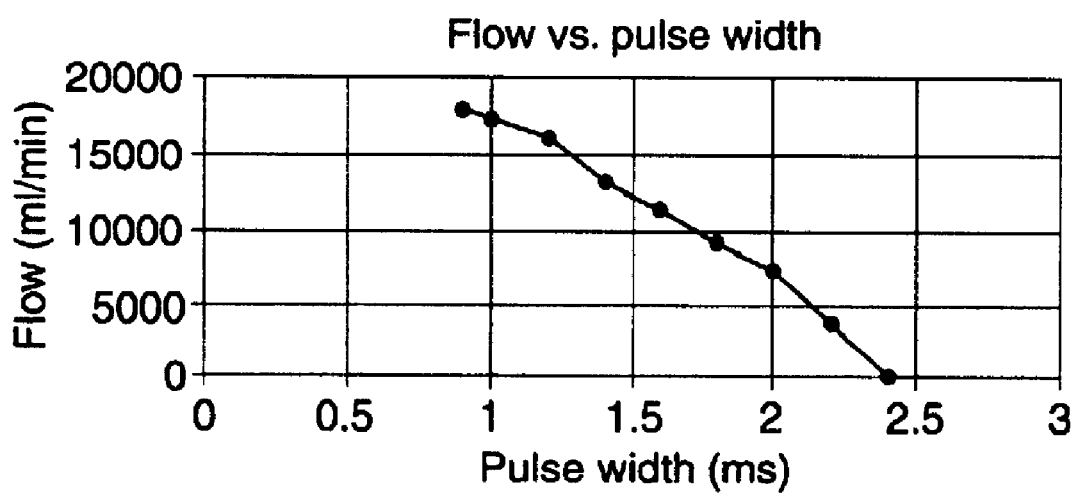
FIG. 3 is a graph of flow versus pulse width in one embodiment of the invention.

One embodiment of the invention uses a high speed, high torque model airplane servomotor 34 controlled by pulse width modulation. A standard computer processor used to control the valve employs a built in pulse generator or, alternatively, sends a voltage from a digital to analog converter to a separate pulse generator circuit. In either case, once an appropriate valve position is obtained, no processor resources are needed to maintain the valve position. FIG. 3 is a graph of flow versus pulse width in one embodiment of the invention. Note that extreme linearity between the valve position and fluid flow is not required, because flow is measured independently downstream of the first fluid outlet 18 and thus the processor is able to compensate for any non-linearity.

In summary, the present invention provides for a low-pressure valve that enables precise linear control of fluid flow through the valve. In addition, the device is compact and inexpensive. While the above description contains many specifics, the reader should not construe these as limitations on the scope of the invention, but merely as examples of specific embodiments thereof. Those skilled in the art will envision many other possible variations that are within its scope. Accordingly, the reader is requested to determine the scope of the invention by the appended claims and their legal equivalents, and not by the specific embodiments given above.

What is claimed is:

1. A low-pressure valve, used in conjunction with a portable ventilator system, comprising:
   a housing having an upstream end and a downstream end, said upstream end having at least one fluid inlet and said downstream end having first and second fluid outlets;
   an orifice plate disposed in said housing, said orifice plate having a first opening for allowing fluid to flow to said first fluid outlet, and a second opening for allowing fluid to flow to said first fluid outlet, and a second opening for allowing fluid to flow to said second fluid outlet;
   a wiper plate disposed parallel to and sealingly adjacent said orifice plate, whereby transverse motion of said wiper plate relative to said orifice plate at least partially covers said first orifice plate opening while it simultaneously at least partially uncovers said second orifice plate opening;
   multiple orifice plate designs;
   means for quick disassembly of said valve housing; and
   means for rapidly substituting one of said multiple orifice plate designs disposed in said valve housing for another depending on the needs of an individual patient.

2. A low-pressure valve as recited in claim 1, further comprising:
   a motor mounted to said valve housing, said motor having a drive shaft perpendicularly engaging said wiper plate whereby axial rotation of said shaft provides axial rotation of said wiper plate.

3. A low-pressure valve as recited in claim 2, wherein said motor is a servomotor.

4. A low-pressure valve as recited in claim 1, wherein said wiper plate includes an elongated transverse slot for enabling gas to pass through said openings in said orifice plate.

5. A low-pressure valve as recited in claim 1, wherein said orifice plate includes a transverse series of holes.

* * * * *

UNITED STATES PATENT AND TRADEMARK OFFICE
CERTIFICATE OF CORRECTION

PATENT NO.   : 6,647,983 B2
DATED        : November 18, 2003
INVENTOR(S)  : Dexter G. Smith et al.

It is certified that error appears in the above-identified patent and that said Letters Patent is hereby corrected as shown below:

<u>Title page,</u>
Item [75], Inventors, delete "Catonsville" and insert therefor -- Yardley --

Signed and Sealed this

Twenty-fifth Day of May, 2004

JON W. DUDAS
*Acting Director of the United States Patent and Trademark Office*